US00PP26924P2

(12) United States Plant Patent
Luo

(10) Patent No.: US PP26,924 P2
(45) Date of Patent: Jul. 12, 2016

(54) ***MANDEVILLA* PLANT NAMED 'DREAMNUFLOR3513'**

(50) Latin Name: *Mandevilla hybrida*
Varietal Denomination: Dreamnuflor3513

(71) Applicant: Shuming Luo, Dulwich Hill (AU)

(72) Inventor: Shuming Luo, Dulwich Hill (AU)

(73) Assignee: Nuflora International Pty, Ltd., Macquarie Fields, NSW (AU)

( * ) Notice: Subject to any disclaimer, the term of this patent is extended or adjusted under 35 U.S.C. 154(b) by 40 days.

(21) Appl. No.: 14/121,806

(22) Filed: Oct. 20, 2014

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Anne Grunberg
(74) *Attorney, Agent, or Firm* — C. A. Whealy

(57) ABSTRACT

A new and distinct cultivar of *Mandevilla* plant named 'Dreamnuflor3513', characterized by its upright and somewhat vining to climbing plant habit; vigorous growth habit; early and freely flowering habit; long flowering period; bright red-colored flowers; and good garden performance.

1 Drawing Sheet

Botanical designation: *Mandevilla hybrida.*
Cultivar denomination: 'DREAMNUFLOR3513'.

CROSS REFERENCED TO CLOSELY-RELATED APPLICATIONS

Title: *Mandevilla* Plant Named 'Dreamnuflor3512'
Applicant: Shuming Luo
Filed: Concurrently with this application having application Ser. No. 14/121,805.

BACKGROUND OF THE INVENTION

The present invention relates to a new and distinct cultivar of *Mandevilla* plant, botanically known as *Mandevilla hybrida* and hereinafter referred to by the name 'Dreamnuflor3513'.

The new *Mandevilla* plant is a product of a planned breeding program conducted by the Inventor in Cobbitty, New South Wales, Australia. The objective of the breeding program is to create new *Mandevilla* plants that flower for a long period of time and have large attractive flowers.

The new *Mandevilla* plant originated from a cross-pollination made by the Inventor in Cobbitty, New South Wales, Australia in February, 2009 of a proprietary selection of *Mandevilla hybrida* identified as code number DIP 799, not patented, as the female, or seed parent with a proprietary selection of *Mandevilla hybrida* identified as code number DIP 7100, not patented, as the male, or pollen, parent. The new *Mandevilla* plant was discovered and selected by the Inventor as a single flowering plant from within the progeny of the stated cross-pollination in a controlled greenhouse environment in Cobbitty, New South Wales, Australia in May, 2010.

Asexual reproduction of the new *Mandevilla* plant by cuttings in Macquarie Fields, New South Wales, Australia since May, 2010 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dreamnuflor3513'. These characteristics in combination distinguish 'Dreamnuflor3513' as a new and distinct *Mandevilla* plant:

1. Upright and somewhat vining to climbing plant habit.
2. Vigorous growth habit.
3. Early and freely flowering habit.
4. Long flowering period.
5. Bright red-colored flowers.
6. Good garden performance.

Plants of the new *Mandevilla* can be compared to plants of the female parent selection. Plants of the new *Mandevilla* differ primarily from plants of the female parent selection in the following characteristics:

1. Plants of the new *Mandevilla* have smaller leaves than plants of the female parent selection.
2. Leaves of plants of the new *Mandevilla* are smooth and glabrous whereas leaves of plants of the female parent selection are pubescent.
3. Plants of the new *Mandevilla* and the female parent selection differ in flower color as plants of the female parent selection have pale pink-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* have larger leaves than plants of the male parent selection.
2. Plants of the new *Mandevilla* and the male parent selection differ in flower color as plants of the male parent selection have darker red-colored flowers.

Plants of the new *Mandevilla* can be compared to plants of 'Dreamnuflor3512', disclosed in a U.S. Plant patent application Ser. No. 14/121,805, filed concurrently. Plants of the new

*Mandevilla* and 'Dreamnuflor3512' differ primarily in flower color as plants of 'Dreamnuflor3512' have dark pink-colored flowers.

Plants of the new *Mandevilla* can be compared to plants of *Mandevilla hybrida* 'White Fantasy', not patented. In side-by-side comparisons conducted in Cobbitty, New South Wales, Australia, plants of the new *Mandevilla* differed primarily from plants of 'White Fantasy' in the following characteristics:

1. Plants of the new *Mandevilla* had smaller leaves than plants of 'White Fantasy'.
2. Leaves of plants of the new *Mandevilla* were smooth and glabrous whereas leaves of plants of 'White Fantasy' were pubescent.
3. Plants of the new *Mandevilla* and 'White Fantasy' differed in flower color as plants of 'White Fantasy' had white-colored flowers.

Plants of the new *Mandevilla* can also be compared to plants of *Mandevilla hybrida* 'Crimson Fantasy', not patented. In side-by-side comparisons conducted in Cobbitty, New South Wales, Australia, plants of the new *Mandevilla* differed primarily from plants of 'Crimson Fantasy' in the following characteristics:

1. Plants of the new *Mandevilla* had smaller leaves than plants of 'Crimson Fantasy'.
2. Leaves of plants of the new *Mandevilla* were smooth and glabrous whereas leaves of plants of 'Crimson Fantasy' were pubescent.
3. Plants of the new *Mandevilla* and 'Crimson Fantasy' differed in flower color as plants of 'Crimson Fantasy' had crimson-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the following detailed botanical description which accurately describe the actual colors of the new *Mandevilla* plant.

The photograph at the bottom of the sheet comprises a side perspective view of a typical flowering plant of 'Dreamnuflor3513' grown in a container.

The photograph at the top of the sheet is a close-up views of a typical flowering plant of 'Dreamnuflor3513'.

DETAILED BOTANICAL DESCRIPTION

The aforementioned photographs and following observations, measurements and values describe plants grown in one-gallon containers during the early summer in a polyethylene-covered greenhouse in Vista, Calif. and under cultural practices typical of commercial *Mandevilla* production. During the production of the plants, day temperatures averaged 27° C. and night temperatures averaged 21° C. Plants were pinched two times and were 19 weeks old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Dreamnuflor3513'.

Parentage:

*Female, or seed, parent*.—Proprietary selection of *Mandevilla hybrida* identified as code number DIP 799, not patented.

*Male, or pollen, parent*.—Proprietary selection of *Mandevilla hybrida* identified as code number DIP 7100, not patented.

Propagation:

*Type*.—By cuttings.

*Time to initiate roots, summer*.—About ten days at temperatures about 25° C. to 30° C.

*Time to initiate roots, winter*.—About 16 days at temperatures about 15° C. to 20° C.

*Time to produce a rooted young plant, summer*.—About four weeks at temperatures about 25° C. to 30° C.

*Time to produce a rooted young plant, winter*.—About six weeks at temperatures about 15° C. to 20° C.

*Root description*.—Medium in thickness, fibrous; white in color becoming creamy white to golden yellow with development.

*Rooting habit*.—Freely branching; dense.

Plant description:

*Plant and growth habit*.—Upright and somewhat vining to climbing plant habit; vigorous growth habit.

*Plant height*.—About 38 cm.

*Plant diameter*.—About 32 cm by 35 cm.

*Lateral branch description*.—Branching habit: Moderate branching habit; pinching enhances lateral branch development; about four primary lateral branches each with numerous secondary branches. Length: About 34 cm. Diameter: About 4 mm. Internode length: About 2.6 cm. Texture: Smooth, glabrous; becoming woody with development. Color: Close to 146A; color becoming closer to 199B with development.

Leaf description:

*Arrangement*.—Opposite, simple.

*Length*.—About 8.5 cm.

*Width*.—About 5.2 cm.

*Shape*.—Elliptical.

*Apex*.—Acuminate.

*Base*.—Equilateral.

*Margin*.—Entire.

*Texture, upper and lower surfaces*.—Smooth, glabrous; leathery.

*Venation pattern*.—Pinnate, arcuate.

*Color*.—Developing leaves, upper surface: Close to 146A. Developing leaves, lower surface: Close to 146B. Fully expanded leaves, upper surface: Close to N137A; venation, close to 147B. Fully expanded leaves, lower surface: Close to 147B; venation, close to 147C.

*Petioles*.—Length: About 1.5 cm. Diameter: About 2 mm. Texture, upper and lower surfaces: Smooth, glabrous. Color, upper and lower surfaces: Close to 146C.

Flower description:

*Flower type and habit*.—Salverform flowers arranged alternately in axillary clusters similar to loose racemes; flowers face horizontally to slightly drooping; freely flowering habit, about eight to ten flowers per cluster and about 60 flowers developing per plant.

*Natural flowering season*.—Early flowering habit, plants begin flowering about four to six weeks after planting; long flowering period, plants flower continuously from late winter into the late autumn in Southern California.

*Flower longevity on the plant*.—About four to five days; flowers not persistent.

*Fragrance*.—None detected.

*Flower buds*.—Height: About 8.3 cm. Diameter: About 1.8 cm. Shape: Elongated oblong to pointed. Color: Close to 61B.

*Cluster height*.—About 11 cm.

*Cluster diameter*.—About 7.5 cm by 9 cm.

*Flower diameter*.—About 6.5 cm.

*Flower depth* (*length*).—About 7.6 cm.

*Flower throat diameter*.—About 1.8 cm.

*Flower tube length*.—About 6.4 cm.

*Flower tube diameter, base*.—About 5 mm.

*Corolla*.—Arrangement and appearance: Single whorl of five petals, petals slightly imbricate; lobes asymmetrical giving a pinwheel appearance to the flower. Petal lobe length: About 3 cm. Petal lobe width: About 3 cm. Petal lobe shape: Asymmetrical; recurved. Petal apex: Acuminate. Petal margin: Entire. Petal texture, upper and lower surfaces: Smooth, glabrous; velvety. Throat texture: Smooth, glabrous. Tube texture: Smooth, glabrous. Color: Petal lobe, when opening, upper surface: Close to 46A. Petal lobe, when opening, lower surface: Close to 53A. Petal lobe, fully opened, upper surface: Slightly striated, close to 46A and 46B; venation, close to 46A; color does not change with development. Petal lobe, fully opened, lower surface: Close to 46A to 46B; venation, close to 46A. Throat: Close to N163A; at throat apex, central ring, close to 54A; venation, close to N163A and 46A. Tube: Proximally, close to 160C; mid-section, close to 1C to 1D; distally, close to 53B; venation, close to 53B and occasionally close to 157D.

*Sepals*.—Arrangement and appearance: Five per flower fused in a single whorl; calyx short funnelform and five-pointed. Length: About 6 mm. Width: About 3 mm. Shape: Lanceolate. Apex: Acuminate. Margin: Entire. Texture, upper and lower surfaces: Smooth, glabrous. Color, upper surface: Close to 145C. Color, lower surface: Close to 145B to 145C.

*Peduncles*.—Length: About 6 cm. Diameter: About 2.5 mm. Texture: Smooth, glabrous. Strength: Strong, flexible. Aspect: About 35° to 45° from lateral branch axis. Color: Close to 146B.

*Pedicels*.—Length: About 1.7 cm. Diameter: About 2 mm. Texture: Smooth, glabrous. Strength: Strong, flexible. Aspect: About 15° to 25° from peduncle axis. Color: Close to 146C.

*Reproductive organs*.—Stamens: Quantity per flower: Typically five. Filament length: About 4 mm. Filament color: Close to 157D. Anther length: About 8 mm. Anther shape: Lanceolate. Anther color: Close to 161B. Pollen amount: None observed. Pistils: Quantity per flower: Typically one. Pistil length: About 2.7 cm. Style length: About 2.1 cm. Style color: Close to 145D. Stigma shape: Rounded. Stigma color: Close to 146D. Ovary color: Close to 144C.

*Seeds and fruits*.—Seed and fruit production has not been observed on plants of the new *Mandevilla*.

Disease & pest tolerance: Plants of the new *Mandevilla* have been observed to be somewhat tolerant to mites. Plants of the new *Mandevilla* have not been noted to be resistant to pathogens and other pests common to *Mandevilla* plants.

Garden performance: Plants of the new *Mandevilla* have been observed to have good garden performance and to tolerate rain, wind, full sunlight and temperatures from about 5° C. to about 45° C.

It is claimed:

1. A new and distinct *Mandevilla* plant named 'Dreamnuflor3513' as illustrated and described.

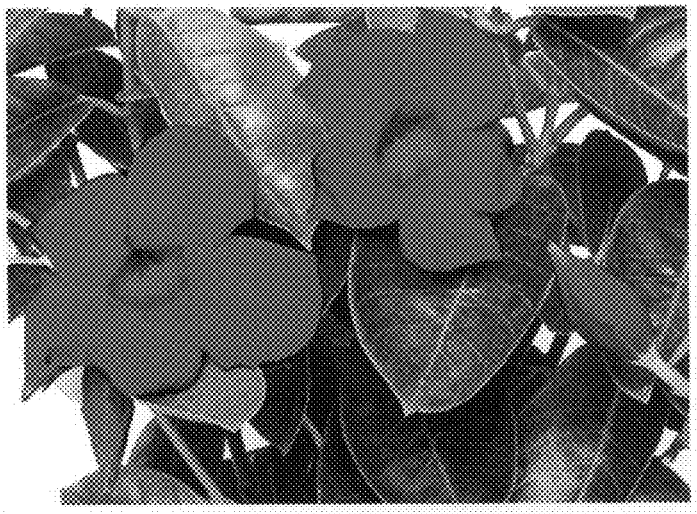
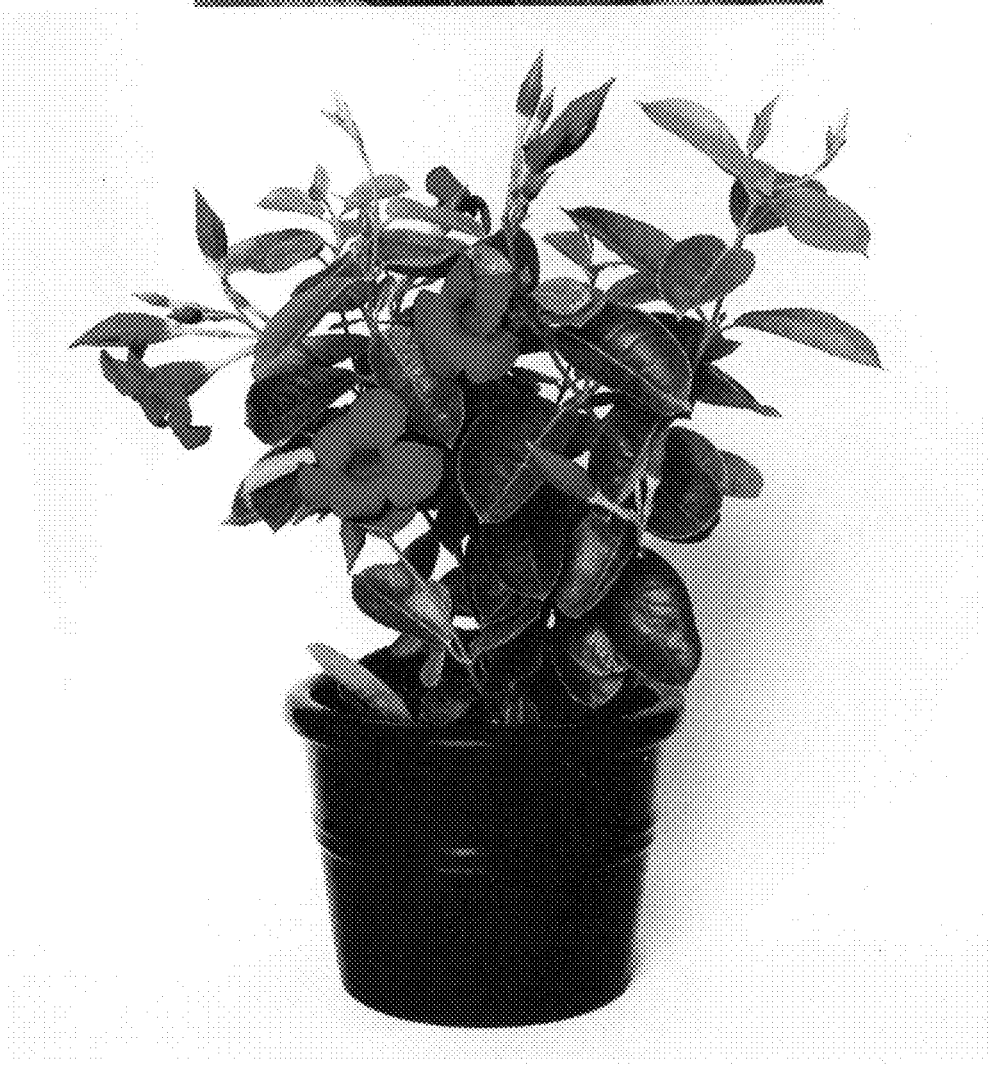

* * * * *